(12) United States Patent
Bouasaysy

(10) Patent No.: US 9,149,611 B2
(45) Date of Patent: Oct. 6, 2015

(54) MATERIALS AND METHODS FOR IMPROVED INTRAGASTRIC BALLOON DEVICES

(75) Inventor: Outhit Bouasaysy, Corona, CA (US)

(73) Assignee: ReShape Medical, Inc., San Clemente, CA (US)

( * ) Notice: Subject to any disclaimer, the term of this patent is extended or adjusted under 35 U.S.C. 154(b) by 495 days.

(21) Appl. No.: 13/577,618

(22) PCT Filed: Feb. 8, 2011

(86) PCT No.: PCT/US2011/024082
§ 371 (c)(1),
(2), (4) Date: Aug. 28, 2012

(87) PCT Pub. No.: WO2011/097637
PCT Pub. Date: Aug. 11, 2011

(65) Prior Publication Data
US 2013/0060274 A1    Mar. 7, 2013

Related U.S. Application Data

(60) Provisional application No. 61/302,465, filed on Feb. 8, 2010.

(51) Int. Cl.
*A61M 29/02* (2006.01)
*A61M 25/10* (2013.01)
(Continued)

(52) U.S. Cl.
CPC .......... *A61M 25/1029* (2013.01); *A61F 5/0036* (2013.01); *A61L 31/10* (2013.01); *A61M 31/00* (2013.01); *A61M 2025/1031* (2013.01); *A61M 2209/02* (2013.01)

(58) Field of Classification Search
USPC ................. 606/191, 192, 193, 194, 195, 198
See application file for complete search history.

(56) References Cited

U.S. PATENT DOCUMENTS

| 2,493,326 | A | 1/1950 | Trinder |
| 4,133,315 | A | 1/1979 | Berman et al. |

(Continued)

FOREIGN PATENT DOCUMENTS

| DE | 8708978 U1 | 11/1987 |
| EP | 0105481 | 3/1984 |

(Continued)

OTHER PUBLICATIONS

European Supplementary Search Report; EP Application No. 10802994.3, Applicant: ReShape Medical, Inc., mailed Jun. 28, 2013, 8 pgs.

(Continued)

*Primary Examiner* — Vy Bui
(74) *Attorney, Agent, or Firm* — Perkins Coie LLP

(57) ABSTRACT

Disclosed is a balloon of an intragastric device, comprising, in combination: a core of a first material and having an inner surface and an outer surface; and a coating of a second material on at least one of the inner surface of the core and the outer surface of the core. Disclosed is a method, comprising, in combination: creating a core of a balloon by a core in a first material; dipping at least one of an inner surface of the core and an outer surface of the core in a second material, whereby a coating is formed on at least one of the inner surface of the core and the outer surface of the core. The first material may be of a more dimensional consistency than the second material, have a greater elasticity than the second material, or be primarily of polydimethyl-siloxane.

9 Claims, 5 Drawing Sheets

(51) Int. Cl.
*A61F 5/00* (2006.01)
*A61L 31/10* (2006.01)
*A61M 31/00* (2006.01)

(56) References Cited

U.S. PATENT DOCUMENTS

| | | | |
|---|---|---|---|
| 4,198,983 A | 4/1980 | Becker et al. |
| 4,246,893 A | 1/1981 | Berson |
| 4,356,824 A | 11/1982 | Vazquez |
| 4,416,267 A | 11/1983 | Garren et al. |
| 4,465,072 A | 8/1984 | Taheri |
| 4,465,818 A | 8/1984 | Shirahata et al. |
| 4,485,805 A | 12/1984 | Foster, Jr. et al. |
| 4,543,089 A | 9/1985 | Moss |
| 4,598,699 A | 7/1986 | Garren et al. |
| 4,694,827 A | 9/1987 | Weiner et al. |
| 4,723,547 A | 2/1988 | Kullas et al. |
| 4,899,747 A | 2/1990 | Garren et al. |
| 4,940,458 A | 7/1990 | Cohn |
| 5,073,347 A | 12/1991 | Garren et al. |
| 5,084,061 A | 1/1992 | Gau et al. |
| 5,123,840 A | 6/1992 | Nates |
| 5,234,454 A | 8/1993 | Bangs |
| 5,259,399 A | 11/1993 | Brown |
| 5,263,934 A | 11/1993 | Haak |
| 5,273,536 A | 12/1993 | Savas |
| 5,318,530 A | 6/1994 | Nelson |
| 5,334,187 A | 8/1994 | Fischell et al. |
| 5,431,173 A | 7/1995 | Chin et al. |
| 5,496,271 A | 3/1996 | Burton et al. |
| 5,516,812 A * | 5/1996 | Chu et al. .................. 522/20 |
| 5,575,772 A | 11/1996 | Lennox |
| 5,639,810 A * | 6/1997 | Smith et al. .................. 524/269 |
| 5,643,209 A | 7/1997 | Fugoso et al. |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,938,669 A | 8/1999 | Klaiber et al. |
| 5,993,473 A | 11/1999 | Chan |
| 5,997,503 A | 12/1999 | Willis et al. |
| 6,149,621 A | 11/2000 | Makihara |
| 6,254,355 B1 | 7/2001 | Gharib |
| 6,276,567 B1 | 8/2001 | Diaz et al. |
| 6,280,411 B1 | 8/2001 | Lennox |
| 6,423,058 B1 | 7/2002 | Edwards et al. |
| 6,427,089 B1 | 7/2002 | Knowlton |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Silverman |
| 6,547,788 B1 | 4/2003 | Maguire et al. |
| 6,579,301 B1 | 6/2003 | Bales et al. |
| 6,592,552 B1 | 7/2003 | Schmidt |
| 6,613,018 B2 | 9/2003 | Bagga et al. |
| 6,613,037 B2 | 9/2003 | Khosravi et al. |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,657 B2 | 3/2005 | Shchervinsky et al. |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,939,299 B1 | 9/2005 | Petersen et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | De la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu |
| 7,828,749 B2 | 11/2010 | Douglas et al. |
| 8,083,757 B2 | 12/2011 | Gannoe et al. |
| 2001/0022988 A1 | 9/2001 | Schwarz et al. |
| 2001/0037127 A1 | 11/2001 | De Hoyos Garza |
| 2002/0055757 A1 | 5/2002 | Torre |
| 2002/0107515 A1 | 8/2002 | Edwards et al. |
| 2002/0161388 A1 | 10/2002 | Samuels et al. |
| 2002/0173804 A1 | 11/2002 | Rousseau |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0059290 A1 | 3/2004 | Palasis |
| 2004/0073162 A1 | 4/2004 | Bleam et al. |
| 2004/0087902 A1 | 5/2004 | Richter |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson et al. |
| 2004/0220665 A1 | 11/2004 | Hossainy et al. |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 * | 2/2005 | Richard et al. ............. 604/890.1 |
| 2005/0027313 A1 | 2/2005 | Shaker |
| 2005/0038415 A1 | 2/2005 | Rohr et al. |
| 2005/0055039 A1 | 3/2005 | Burnett et al. |
| 2005/0059990 A1 | 3/2005 | Ayala |
| 2005/0075624 A1 | 4/2005 | Miesel |
| 2005/0085792 A1 | 4/2005 | Gershowitz |
| 2005/0119674 A1 | 6/2005 | Gingras et al. |
| 2005/0131442 A1 | 6/2005 | Yachia et al. |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192614 A1 | 9/2005 | Binmoeller |
| 2005/0192615 A1 | 9/2005 | Torre et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0058829 A1 | 3/2006 | Sampson et al. |
| 2006/0178691 A1 | 8/2006 | Binmoeller |
| 2006/0184112 A1 | 8/2006 | Horn et al. |
| 2006/0259020 A1 | 11/2006 | Sharratt |
| 2007/0016262 A1 | 1/2007 | Gross et al. |
| 2007/0078476 A1 | 4/2007 | Hull et al. |
| 2007/0093728 A1 | 4/2007 | Douglas et al. |
| 2007/0100367 A1 | 5/2007 | Quijano |
| 2007/0100368 A1 | 5/2007 | Quijano |
| 2007/0100369 A1 | 5/2007 | Cragg |
| 2007/0135829 A1 | 6/2007 | Paganon |
| 2007/0142770 A1 | 6/2007 | Rioux et al. |
| 2007/0149994 A1 | 6/2007 | Sosnowski |
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0190363 A1 | 8/2008 | Chen et al. |
| 2008/0208135 A1 | 8/2008 | Annunziata |
| 2008/0208241 A1 | 8/2008 | Weiner et al. |
| 2008/0233167 A1 | 9/2008 | Li et al. |
| 2008/0243071 A1 | 10/2008 | Quijano |
| 2008/0243166 A1 | 10/2008 | Paganon et al. |
| 2008/0255601 A1 | 10/2008 | Birk |
| 2008/0319471 A1 | 12/2008 | Sosnowski et al. |
| 2009/0048624 A1 | 2/2009 | Alverdy |
| 2009/0259236 A2 | 10/2009 | Burnett et al. |

(56) References Cited

U.S. PATENT DOCUMENTS

| | | | |
|---|---|---|---|
| 2009/0275973 | A1 | 11/2009 | Chen et al. |
| 2010/0023047 | A1 | 1/2010 | Simpson |
| 2010/0130998 | A1 | 5/2010 | Alverdy |
| 2010/0243135 | A1 | 9/2010 | Pepper et al. |
| 2011/0178544 | A1 | 7/2011 | Sosnowski et al. |
| 2012/0271336 | A1 | 10/2012 | Hamman et al. |
| 2012/0289992 | A1 | 11/2012 | Quijano et al. |

FOREIGN PATENT DOCUMENTS

| | | |
|---|---|---|
| EP | 0457456 | 5/1990 |
| EP | 0485903 | 8/1991 |
| EP | 1781183 | 5/2007 |
| FR | 2862525 | 5/2005 |
| FR | 2892297 | 4/2007 |
| GB | 2090747 A | 7/1982 |
| GB | 2139902 | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| WO | WO9000369 | 1/1990 |
| WO | WO9925418 | 5/1999 |
| WO | WO-0141700 | 6/2001 |
| WO | WO-0166166 A2 | 9/2001 |
| WO | WO-0240081 | 5/2002 |
| WO | WO2006035446 | 4/2006 |
| WO | WO2006056944 | 6/2006 |
| WO | WO2006/128978 | 12/2006 |
| WO | WO-2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO2008121831 | 10/2008 |
| WO | WO-2009055386 A2 | 4/2009 |
| WO | WO2009112786 | 9/2009 |
| WO | WO-2010048021 | 4/2010 |
| WO | WO2010115161 | 10/2010 |
| WO | WO2011011629 | 1/2011 |
| WO | WO2011011741 | 1/2011 |
| WO | WO2011011743 | 1/2011 |
| WO | WO2011038270 | 3/2011 |
| WO | WO2011024077 | 8/2011 |
| WO | WO2011097637 | 8/2011 |
| WO | WO2011127205 | 10/2011 |
| WO | WO2012048226 | 4/2012 |

OTHER PUBLICATIONS

European Supplementary Search Report; EP Application No. 10802918.2, Applicant: ReShape Medical, Inc., mailed Jun. 5, 2013, 6 pgs.

Extended European Search Report; Application No. EP6827098.3, Applicant: Reshape Medical, Corporation, mailed on Aug. 25, 2014, 3 pages.

Extended European Search Report; Application No. EP6827314.3, Applicant: ReShape Medical Corporation mailed Aug. 1, 2014, 3 pages.

Extended European Search Report; Application No. EP6827313.5, Applicant: ReShape Medical Corporation, mailed Jul. 30, 2014, 5 pages.

Extended European Search Report; Application No. EP6847847.8, Applicant ReShape Medical Corporation, mailed Aug. 14, 2014, 5 pages.

Final Office Action; U.S. Appl. No. 13/858,767, mailed on May 30, 2014, 12 pages.

Non-Final Office Action; U.S. Appl. No. 13/386,638, mailed on Jun. 27, 2014, 12 pages.

Extended European Search Report; Application No. EP11766679.2, Applicant: Reshape Medical, Inc., mailed Dec. 12, 2013, 6 pages.

Extended European Search Report; Application No. EP11748141.6, Applicant: Reshape Medical, Inc., mailed Feb. 25, 2014, 6 pages.

European Search Report—Supplementary; EP 03726447.0, Applicant: Applied Medical Resources Corporation: Mar. 1, 2006, 3 pgs.

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043134; Applicant: ReShape Medical, Inc., Mailing Date Apr. 27, 2011, 12 pages.

International Search Report; International Application No. PCT/US2010/043136; Applicant: ReShape Medical, Inc., Mailing Date Apr. 12, 2011, 9 pages.

International Search Report; International Application No. PCT/US2010/050260; Applicant: ReShape Medical, Inc., Mailing Date: Jun. 17, 2011, 9 pages.

International Search Report; International Application No. PCT/US2011/026233; Applicant: ReShape Medical, Inc., Mailing Date Apr. 26, 2011, 9 pages.

International Search Report; International Application No. PCT/US2011/031463; Applicant: ReShape Medical, Inc., Mailing Date: Jun. 27, 2011, 10 pages.

International Search Report; International Application No. PCT/US2003/012782, Applicant: Applied Medical Resources Corporation, dated: Oct. 28, 2003, 7 pages.

International Search Report; International Application No. PCT/US2006/042336, Applicant: Abdominus, Inc., dated: Mar. 14, 2007, 9 pages.

International Search Report; International Application No. PCT/US2006/042710, Applicant: Abdominus, Inc. et al., dated: Mar. 15, 2007, 9 pages.

International Search Report; International Application No. PCT/US2006/042711, Applicant: Abdominus, Inc. et al, dated: Mar. 16, 2007, 9 pages.

International Search Report; International Application No. PCT/US2006/048647, Applicant: Abdominus, Inc. et al., dated: May 22, 2007, 12 pages.

International Search Report; International Application No. PCT/US2008/058677, Applicant: ReShape Medical et al., dated: Aug. 21, 2008, 12 pages.

International Search Report; International Application No. PCT/US2008/068058, Applicant: ReShape Medical, Inc. et al, dated: Nov. 19, 2008, 11 pages.

International Search Report; International Application No. PCT/US2010/029865, Applicant: ReShape Medical, Inc., dated: Jan. 5, 2011, 9 pages.

International Search Report; International Application No. PCT/US2011/024077; Applicant: ReShape Medical, Inc., dated: Apr. 6, 2011, 12 pages.

International Search Report; International Application No. PCT/US2011/024082, Applicant: ReShape Medical, Inc., dated: Apr. 6, 2011, 10 pages.

International Search Report; International Application No. PCT/US1155373, Applicant: Reshape Medical, Inc., dated: Jan. 20, 2012, 7 pages.

"Living with the BIB: BioEnterics Intragastric Balloon Program: Patient Information"; INAMED Health: Bioenteris Corporation, ECO-SBA-10434; dated Apr. 20, 2004 and May 14, 2005, located online at: www.sydneyobesity.com.au/pdf/M946-01.pdf; 10 pages.

Non-Final Office Action; U.S. Appl. No. 11/694,536; dated: Oct. 26, 2011, 13 pages.

Non-Final Office Action; U.S. Appl. No. 12/723,545; dated Feb. 29, 2012, 10 pages.

Non-Final Office Action; U.S. Appl. No. 12/625,473; dated Oct. 24, 2011, 18 pages.

Non-Final Office Action; U.S. Appl. No. 12/625,473; dated Jul. 12, 2012; 10 pages.

(56) References Cited

OTHER PUBLICATIONS

"ReShape Inflatable Gastric Balloon Going on Trial as Weight Loss Option," MedGadget: Internet Journal of Emerging Medical Technologies. Feb. 4, 2010, 5 pages.
Extended European Search Report; Application EP11740536.5, Applicant: ReShape Medical, Inc. mailed Jul. 3, 2014, 8 pages.
Extended European Search Report; Application EP11831683.5, Applicant: Reshape Medical, Inc., mailed Jul. 3, 2014, 8 pages.
Final Office Action; U.S. Appl. No. 13/556,032, mailed on Jan. 28, 2014, 8 pages.
Non-Final Office Action; U.S. Appl. No. 13/386,650; mailed on Jun. 3, 2014, 15 pages.
Notice of Allowance; U.S. Appl. No. 12/753,803, dated May 13, 2014, 18 pages.
Ostrovsky, ReShape Inflatable Gastric Balloon going on Trial as Weight Loss Option; http://www.medgadget.com/2010/02/reshape_inflatable_gastric_balloon_system_going_on_trial_as_weight_loss_option.html Feb. 4, 2010, retrieved on Feb. 10-13.
Final Office Action; U.S. Appl. No. 13/858,767, Mailing Date May 22, 2103, 12 pages.
Extended European Search Report; Application No. 08732989.2, Applicant: Reshape Medical, Inc., mailed Oct. 16, 2014, 7 pages.
European Examination Report; Application No. EP108002918.2, Applicant: Reshape Medical Inc., mailed Dec. 17, 2014, 5 pages.
European Examination Report; Application No. EP10802994.3, Applicant: Reshape Medical Inc., mailed Dec. 18, 2014, 4 pages.
Japanese Office Action; Application No. 2013-43712, mailed Jan. 8, 2015, 8 pages.
Canadian Office Action; Application No. 2,638,988, mailed Dec. 22, 2014, 3 pages.
Japanese Office Action; Application No. 2014-52972; mailed Feb. 25, 2015, 7 pages.
Canadian Office Action; Application No. 2,691,530, mailed Dec. 18, 2014, 4 pages.
Canadian Office Action; Application No. 2,638,163, mailed Mar. 10, 2015, 4 pages.
European Supplementary Search Report; Application No. 08771842.5, Apr. 4, 2015, 3 pages.
Non-Final Office Action; U.S. Appl. No. 11/263,302; dated: Oct. 9, 2012, 6 pages.
Non-Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
Wahlen Ch et al. "The BioEnterics Intragastric Balloon: How to use it" Obesity Surgery 2001; 11:524-527.

\* cited by examiner

MATERIALS AND METHODS FOR IMPROVED INTRAGASTRIC BALLOON DEVICES

CROSS-REFERENCE TO RELATED APPLICATION

The present application claims priority under 35 U.S.C. 371 of International Application Ser. No. PCT/US2011/024082, filed Feb. 8, 2011, which claims the benefit of U.S. Provisional Patent Application Ser. No. 61/302,465, filed Feb. 8, 2010, the entire contents of which is incorporated herein by reference in their entireties.

RELATED REFERENCES

This application incorporates by reference: U.S. Pat. Pub. No. 2007/0100367, published May 3, 2007; U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; U.S. Pat. Pub. No. 2008/0243071, published Oct. 2, 2008; U.S. Pat. Pub. No. 2008/0319471, published Dec. 25, 2008; U.S. Pat. Pub. No. 2005/0159769, published Jul. 21, 2005; U.S. Pat. Pub. No. 2009/0048624, published Feb. 19, 2009; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; each as if fully set forth herein in its entirety.

BACKGROUND

This disclosure relates to implantable, expandable gastric devices. In particular, this disclosure relates to improved structures of balloons and methods of producing the same.

Many conventional implantable gastric devices have a balloon filled with a biocompatible fluid. Such gastric devices are generally inserted into the stomach when the balloon is deflated and then inflated in vivo. The gastric devices are often left in the stomach for an extended period of time to treat severe obesity or other conditions. The gastric devices are eventually removed after completing the treatment or for other reasons by deflating the balloon, grasping the gastric device with an extraction tool, and extracting the gastric device via the esophagus and mouth. Conventional gastric devices are deflated by attempting to puncture the balloon and aspirate the biocompatible fluid through a needle.

One challenge of conventional devices is that the balloon are generally fairly large in a deflated state because of the limited elasticity and expansion of the materials that can withstand the harsh environment within the stomach rupture. Many existing balloons for intragastric devices are made from polydiphenylsiloxane (PDPS), which resists degradation by acids, fungal growth and other microbial growth, but it has limited expansion. As such, the cuffs of such a balloon must have a fairly large diameter so that the balloon can be removed from a mandrel during the manufacturing process.

Another challenge of conventional intragastric devices is the life span of the balloon. For example, fungi or other microbes can grow into the material of the balloon and effectively decrease the wall thickness. This can weaken the balloon wall to the point that it ruptures under the pressure of the fluid in the balloon.

BRIEF DESCRIPTION OF THE DRAWINGS

Several embodiments of the present technology will become more apparent with reference to the following description taken in conjunction with the accompanying drawings wherein like reference numerals denote like elements and in which.

DETAILED DESCRIPTION

Specific details of several embodiments of the present technology are described below with reference to an intragastric device with compound balloon. Although many of the embodiments are described below with respect to a dual balloon intragastric device, other types of devices with only one balloon or more than two balloons may be within the scope of the technology. Moreover, several other embodiments of the technology can have different configurations, components, or procedures than those described in this section. A person of ordinary skill in the art, therefore, will accordingly understand that the technology may have other embodiments with additional elements, or the technology may have other embodiments without several of the features shown and described below with reference to FIGS. 1-7.

Several embodiments of the technology are directed to a balloon of an intragastric device comprising, in combination, a substrate or core of a first material that has having an inner surface and an outer surface, and a coating of a second material on at least one of the inner or outer surfaces. The substrate, for example, can be more elastic and/or have more expansion than the coating, and the coating can be more resistant to fungal or other microbial growth than the substrate.

Additional embodiments of the technology are directed to a method comprising, in combination, forming a core or substrate of a first material into a balloon and covering at least one of an inner surface and/or outer surface of the substrate with a second material. The second material can be a coating that is sprayed, painted or applied by dipping the substrate into the second material, to form a smoother surface finish, as compared to a surface finish of a molded core, having a roughness from about 0.1 to 0.7 micron. This further inhibits or otherwise impedes the formation of biofilm (e.g., candida) on the coated surface of the balloon. Also disclosed are products by processed disclosed herein.

The first material may be of a more dimensionally stable or consistant than the second material and/or have a greater elasticity than the second material. In one embodiment, the first material comprises polydimethylsiloxane (PDMS). The second material may have a higher resistance to acid, be more resistant to fungal or other microbial activity, and be less permeable than the first material. In one embodiment, the second material comprises PDPS.

Figure 1:
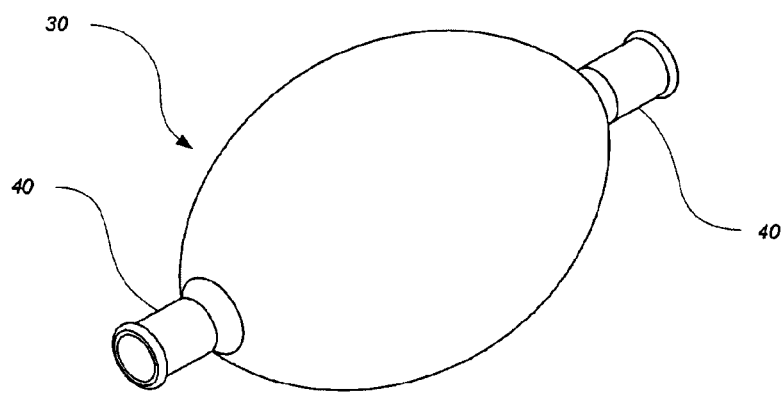
FIG. 1 shows a perspective view of a balloon.
Figure 2:
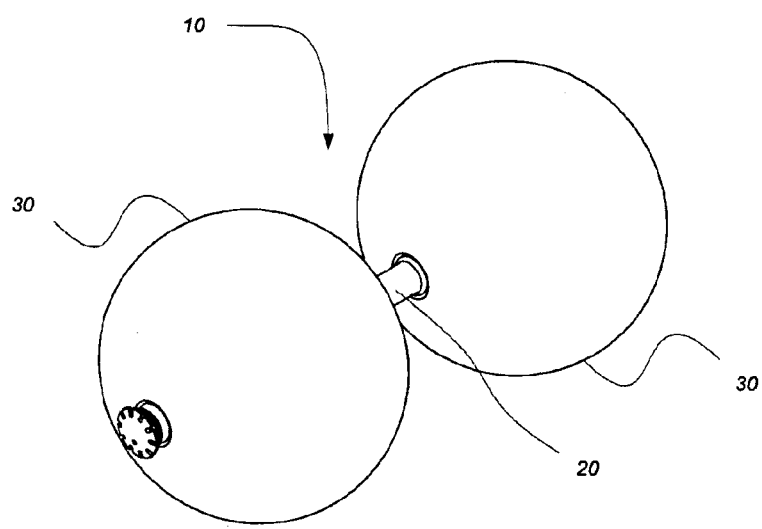
FIG. 2 shows a perspective view of an intragastric device.

In the specific embodiment shown in FIG. 1, a balloon 30 can be one of several expandable, space filling components. In several embodiments, and as shown in FIG. 2, the balloon 30 may be a component of an intragastric device 10. For example, as further shown in FIG. 2, the intragastric device 10 can have a shaft 20 and a plurality of the balloons 30 may be joined or otherwise carried by the shaft 20.

Figure 3:
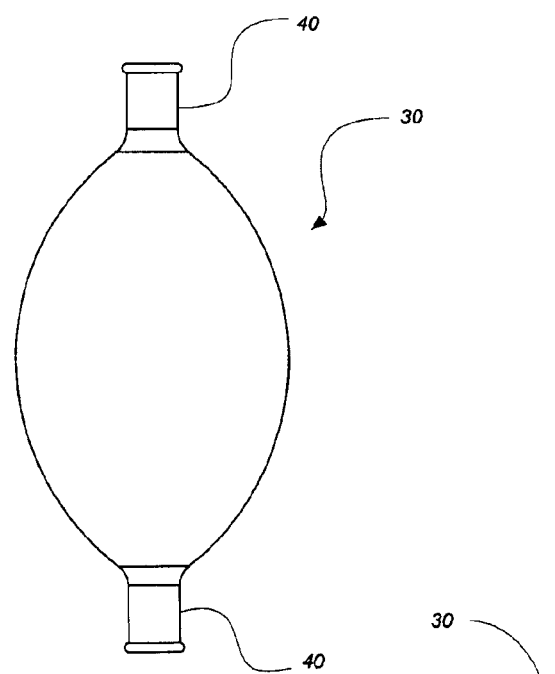
FIG. 3 shows a side view of an intragastric device.
Figure 4:
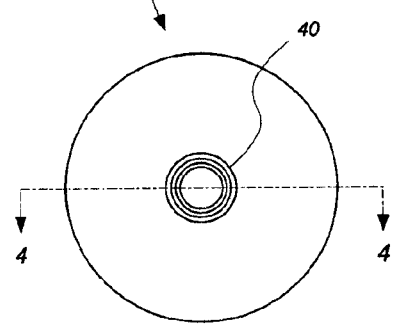
FIG. 4 shows a top view of an intragastric device.

The balloon 30 may have many different geometries and shapes according to the specific anatomy in which the balloon 30 is implanted. As shown in FIGS. 1 and 3, the balloon 30 may have at least one cuff 40 for interfacing with the shaft 20 (FIG. 2) such that the shaft 20 extends through the balloon 30. The balloon 30 may be an open or closed balloon, and the balloon 30 may have an inner surface and outer surface.

According to several embodiments of the technology, the intragastric device 10 may be configured for use as an implantable device within a gastric cavity. In many applications, the intragastric device 10 is implanted for several months in the stomach or other gastric cavity having high concentrations of acids and microbes that can deteriorate the balloon 30. The durability and longevity of the intragastric device 10 is accordingly defined, at least in part, by the ability of the balloon 30 to resist the harsh environment within the stomach. As such, the materials and manufacturing methods of the materials are key contributors as to balloon integrity and longevity.

According to embodiments, the balloon 30 may comprise a combination of two different silicone-containing materials. Two examples of such materials are PDMS and PDPS. PDMS may be represented as $[SiO(CH_3)_2]_n$ or graphically as follows:

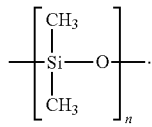

PDPS may be represented as $[SiO(C_6H_5)_2]_n$ or graphically as follows:

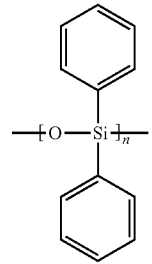

According to several embodiments of the technology, at least one of PDMS and PDPS may form the substrate or core of at least a portion of the balloon 30. Other materials, structures, or compounds may be mixed or cross-linked with the based material.

According to several embodiments of the technology, a plasma etching or coating may be provided to at least a portion of the balloon 30. Plasma etching may involve a high-speed stream of glow discharge (plasma) of an appropriate gas mixture being shot (in pulses) at a sample. The plasma source can be either charged (ions) or neutral (atoms and radicals). During the process, the plasma will generate volatile etch products at room temperature from the chemical reactions between the elements of the material etched and the reactive species generated by the plasma. The atoms of the shot element embed themselves at or just below the surface of the target, thus modifying the physical properties of the balloon 30. Etching may facilitate better adherence between layers of the balloon 30.

According to several embodiments of the technology, various coatings (e.g., hydrophilic) may be applied to at least a portion of substrate or core of the balloon 30. For example, a hydrophilic coating may be provided where two surfaces of the balloon 30 resist flow of fluid there through.

The respective chemical structures of PDMS and PDPS have relatively disparate characteristics, which may be summarized as follows:

|  | Polydimethylsiloxane | Polydiphenylsiloxane |
|---|---|---|
| Manufacturing method: | Molding, extrusion | Dipping |
| Curing: | Heat | Heat |
| Consistency: | More dimensional (moldable) | Less dimensional (dipping) |
| Elasticity: | Higher | Lower |
| Tensile Strength: | Lower | Higher |
| Acid resistance: | Acceptable | Increased |
| Permeability: | Higher | Lower |

In various applications and based on different aspects, each of PDMS and PDPS may be seen as providing certain advantages and disadvantages.

According to several embodiments of the technology, the dimensional stability or consistency and elasticity of PDMS materials and PDMS blends enable the balloon 30 to be formed using molding and extrusion processes instead of a dipping process. In particular, molding processes include molding the PDMS material over a mandrel, and the higher elasticities of PDMS materials compared to PDPS materials reduce the stresses involved in removing the mandrel. For example, the balloon 30 may be formed using a mandrel that has a larger diameter at a central portion than at one or both ends (corresponding to cuffs 40). For example, the diameter at the middle of a mandrel may be up to 600% larger than at the end of the mandrel. The balloon 30 must sufficiently elastic to remove the mandrel through the cuff 40 without damaging the cuff 40.

According to several embodiments of the technology, the expansion ratio of the balloon 30 from an uninflated state (i.e., before and during implant) to an inflated state (i.e, after implant) may be significant. For example, the balloon 30 may have an outer diameter of about 1.9" in an uninflated state and about 4" in an inflated state (over 200% expansion). By further example, the balloon 30 may have a volume of about 80 cc in an uninflated state and about 450 cc in an inflated state (over 500% expansion). These factors are well-served by PDMS materials and PDMS blends. As such, PDMS and PDMS blends are well suited for the substrate or core of the balloon 30.

In accordance with several embodiments of the invention, the higher acid resistance and less permeability of PDPS materials and PDPS blends, compared to PDMS based materials, better limit the ingress or egress of materials across the walls of the balloon 30 and support longevity of the balloon 30. Generally, PDPS, as compared to PDMS, is less able to provide consistent wall thicknesses and is less capable of generating molding friendly features, but more capable of resisting acids and growth of fungi or bacteria.

In several specific embodiments of the technology, the balloon 30 has a multiple-material composition in which a plurality of disparate materials and material blends may be provide in layers forming walls of the balloon 30. For example, a wall of the balloon 30 may have a substrate or core with at least one coating on an inner or outer surface thereof.

Figure 5:
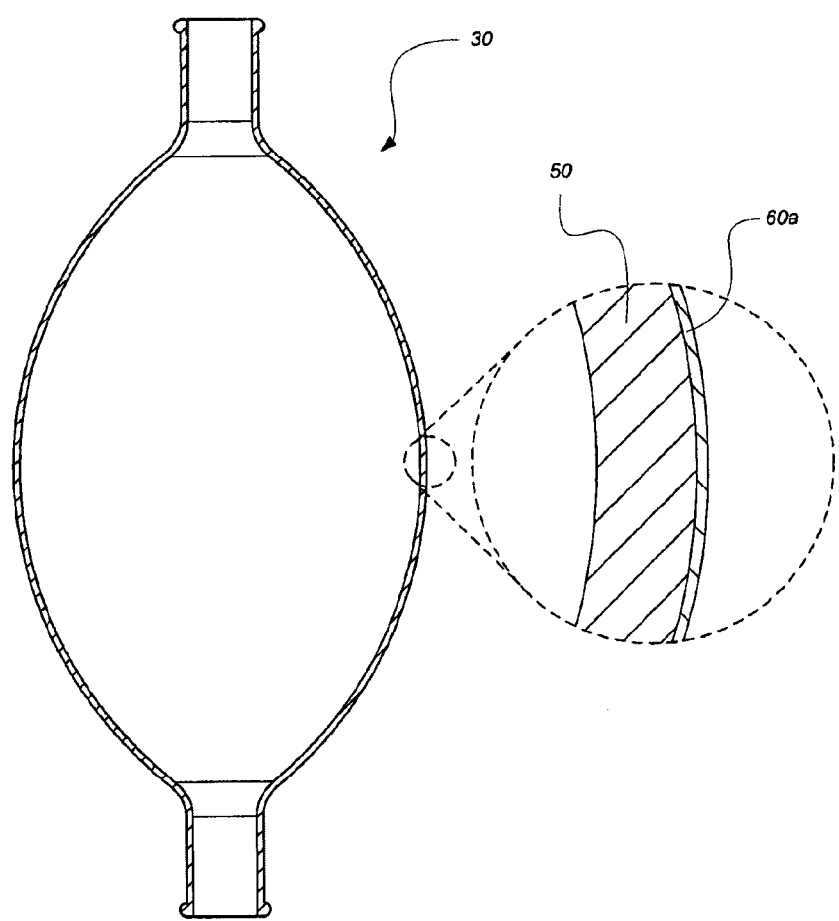
FIG. 5 shows a sectional view of a balloon with a magnified view.
Figure 6:
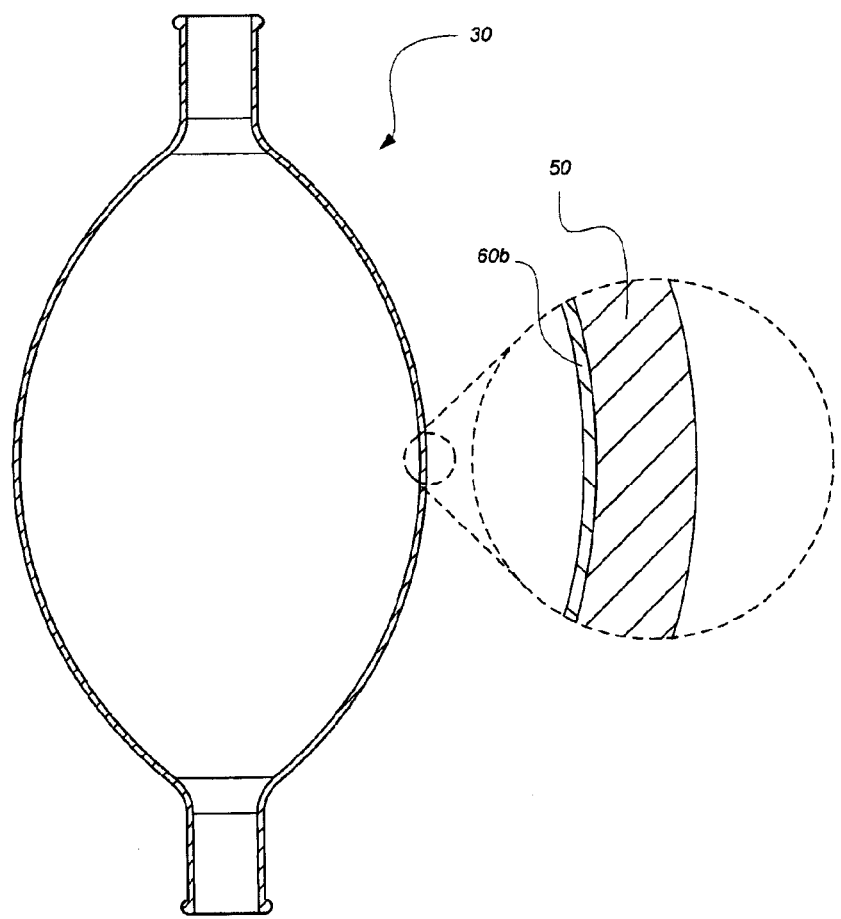
FIG. 6 shows a sectional view of a balloon with a magnified view.

FIGS. 5 and 6 illustrate specific embodiments of the technology. In the embodiment shown in FIG. 5, the balloon can have a substrate or core 50 and outer coating 60a over an outer surface of the core 50. The outer coating 60*a* may be provided, for example, by a dipping process after core 50 is formed. In the embodiment shown in FIG. 6, the balloon 30 can have in inner coating 60*b* over an inner surface of the core 50. The inner coating 60*b* may be provided, for example, by a dipping process after core 50 is formed and the balloon inverted inside-out.

Figure 7:
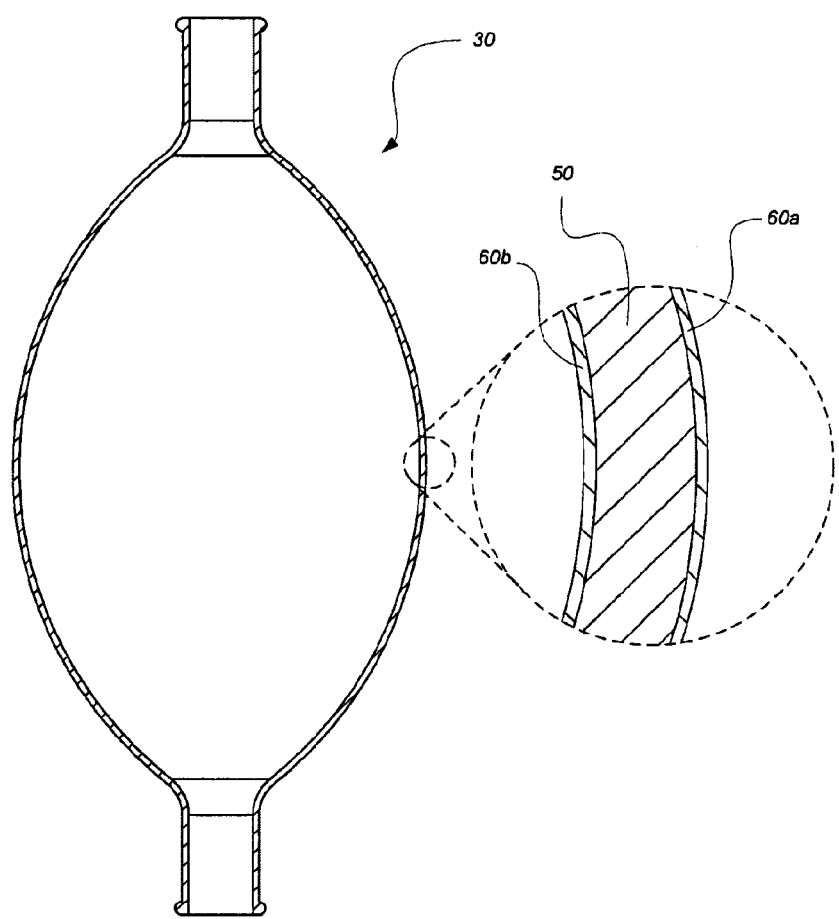
FIG. 7 shows a sectional view of a balloon with a magnified view.

FIG. 7 illustrates another embodiment in which the balloon has the substrate or core 50, the outer coating 60*a* over the outer surface of the core, and an inner coating 60*b* over the inner surface of the core 50. The outer coating 60*a* and inner coating 60*b* may be provided, for example, by a dipping process after core 50 is formed.

In selected embodiments, the substrate or core 50 can comprise PDMS or another material that is moldable and has a higher elasticity than PDPS. The inner and/or outer coatings 60*a-b* can comprises PDPS or another material that is less permeable and more acid resistant than PDMS. According to several embodiments, the balloon 30 having a layered, multiple-material composition may benefit from the advantaged of each material while mitigating or minimizing the detriments of each.

The present technology is also directed to methods of making the balloon 30 is disclosed. In one embodiment, the substrate or core 50 may be molded of the first material, such as a liquid silicone rubber (LSR) grade material (e.g., such as PDMS). Those skilled in the art will recognize various molding and extrusion processes that may facilitate formation of core 50. The molding process can include injecting PDMS or a PDMS blend into a mold such that the molded material surrounds a mandrel or other form. After curing, the core 50 is removed from the mold, mandrel, or other device, and then the second material may be coated onto the inner and/or outer surface of the core 50. For example, the core 50 may be dipped in the second material to form at least one of the outer coating 60*a* and/or the inner coating 60*b*. Other embodiments of the method, the core 50 may be coated using other techniques, such as spraying, painting, coating, washing, etc. The second material can be PDPS or another suitable low-permeable, acid and fungal resistant material.

The core 50 may compose a substantial portion of the total sum of the balloon 30 or at least the walls thereof. For example, the thickness of core 50 may be about 0.001 inch to about 1.0 inch. By further example, the thickness of core 50 may be about 0.024 inch to about 0.030 inch. The core 50 can have other thicknesses based on the needs and applications of the desired product.

The outer coating 60*a* or the inner coating 60*b* may be a thin relative to the thickness of core 50. For example, the outer coating 60*a* or the inner coating 60*b* may have a thickness of about 1% to about 99% of the thickness of core 50. By further example, the outer coating 60*a* or the inner coating 60*b* may have a thickness of about 10% to about 20% of the thickness of core 50. The inner and outer coating 60*a-b* can have other thicknesses based on the needs and applications of the desired product. It should be noted that outer coating 60*a* or inner coating 60*b* comprising PDPS materials increase the stiffness of the balloon 30 and reduce elongation properties thereof.

In still additional embodiments of the technology, the core 50 and/or the coating 60 can include anti-microbial or other additives to impart additional therapeutic, durability, or other properties to the balloon 30. For example, such additives can be distributed homogeneously in the coating 60, or the additives can be a constituent of another coating applied directly to the core 50 or to the coating 60. When such an additional coating is applied directly to the core 50, the coating 60 can be applied onto the other coating. In several specific examples, the additives can comprise salt or silver-based anti-microbial materials that inhibit the growth of microbes on and/or into the core 50.

The multi-layered construction of first and second materials of several embodiments of the balloon may have a substantially consistent surface and retain elastic material properties, increased acid resistance, and lower permeability. For example, the first material of the core 50 can provide good elasticity enable molding processes that provide a controlled wall thickness, and the second material of the coating 60 can provide good resistance to acid, fungus, bacteria and other microbes. The second material of the coating 60 can also have a low permeability.

Although the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An intragastric balloon, comprising, in combination:
   a core of a first material and having an inner surface and an outer surface; and
   a coating of a second material on at least one of the inner surface of the core and the outer surface of the core, wherein the first material is more elastic than the second material and the second material has a lower permeability than the first material, and wherein the second material comprises polydiphenylsiloxane.

2. The intragastric balloon of claim 1, further comprising two cuffs configured to receive a shaft extended through the intragastric balloon.

3. The intragastric balloon of claim 1, wherein the first material is of a more dimensional consistency than the second material.

4. The intragastric balloon of claim 1, wherein the first material has a viscosity suitable for molding processes.

5. The intragastric balloon of claim 1, wherein the first material is primarily of polydimethylsiloxane.

6. The intragastric balloon of claim 5, wherein the second material has higher acid resistance than the first material.

7. The intragastric balloon of claim 1, wherein the second material is less permeable than the first material.

8. The intragastric balloon of claim 1, wherein the intragastric balloon has an expansion ratio of at least about 200% by diameter and at least about 500% by volume.

9. An intragastric device, comprising, in combination:
   a shaft; and
   at least a first balloon fixed to the shaft, the first balloon having a core of a first material and a coating of a second material, the second material comprising polydiphenylsiloxane, wherein the core has an inner surface and an outer surface, and the coating is on at least one of the inner surface of the core and the outer surface of the core, and wherein the first material comprises polydimethylsiloxane.

* * * * *